United States Patent
Takahashi

(10) Patent No.: US 9,044,206 B2
(45) Date of Patent: Jun. 2, 2015

(54) PULSE DETECTOR

(75) Inventor: Yusuke Takahashi, Matsumoto (JP)

(73) Assignee: Seiko Epson Corporation, Tokyo (JP)

( * ) Notice: Subject to any disclaimer, the term of this patent is extended or adjusted under 35 U.S.C. 154(b) by 773 days.

(21) Appl. No.: 13/400,951

(22) Filed: Feb. 21, 2012

(65) Prior Publication Data

US 2012/0220881 A1      Aug. 30, 2012

(30) Foreign Application Priority Data

Feb. 28, 2011   (JP) ................................ 2011-041490

(51) Int. Cl.
  *A61B 5/024*   (2006.01)
  *A61B 5/00*    (2006.01)

(52) U.S. Cl.
  CPC .............. *A61B 5/721* (2013.01); *A61B 5/7207* (2013.01); *A61B 5/024* (2013.01); *A61B 5/02416* (2013.01); *A61B 5/02438* (2013.01); *A61B 5/681* (2013.01)

(58) Field of Classification Search
  CPC .............. A61B 5/024; A61B 5/02416; A61B 5/02433; A61B 5/02438; A61B 5/02444; A61B 5/0245; A61B 5/02455; A61B 5/025; A61B 5/0255; A61B 5/7203; A61B 5/7207; A61B 5/721; A61B 5/7214; A61B 5/7217; A61B 5/725; H03H 21/0012
  See application file for complete search history.

(56) References Cited

U.S. PATENT DOCUMENTS

| | | | | |
|---|---|---|---|---|
| 4,238,746 A | * | 12/1980 | McCool et al. ............... | 333/166 |
| 6,687,723 B1 | * | 2/2004 | Ding .............................. | 708/322 |
| 8,758,258 B2 | * | 6/2014 | Takahashi et al. ............. | 600/483 |
| 2003/0212336 A1 | * | 11/2003 | Lee et al. ....................... | 600/504 |
| 2004/0138538 A1 | * | 7/2004 | Stetson .......................... | 600/310 |
| 2007/0060827 A1 | * | 3/2007 | Kobayashi et al. ............ | 600/500 |
| 2010/0198087 A1 | * | 8/2010 | Takahashi et al. ............. | 600/500 |
| 2011/0098582 A1 | * | 4/2011 | Takahashi et al. ............. | 600/500 |
| 2012/0215115 A1 | | 8/2012 | Takahashi | |

FOREIGN PATENT DOCUMENTS

| | | |
|---|---|---|
| JP | 2005-198829 A | 7/2005 |
| JP | 2007-054471 A | 3/2007 |
| JP | 2010-172645 A | 8/2010 |
| JP | 2011-087838 A | 5/2011 |
| JP | 2011-092236 A | 5/2011 |
| JP | 2011-212383 A | 10/2011 |
| JP | 2011-212384 A | 10/2011 |
| JP | 2012-170701 A | 9/2012 |
| JP | 2012-170703 A | 9/2012 |
| JP | 2012-179209 A | 9/2012 |
| JP | 2012-183139 A | 9/2012 |

* cited by examiner

*Primary Examiner* — Navin Natnithithadha
*Assistant Examiner* — Meredith Weare
(74) *Attorney, Agent, or Firm* — Global IP Counselors, LLP

(57) ABSTRACT

A pulse detector (100) includes a pulse wave sensor (10); a pulse wave signal filtering section (200) having a first adaptive filter (202a) and second adaptive filter (202b), and an adaptive filter switching section (17); and a pulse wave frequency analyzer (400), wherein the adaptive filter switching section (17) starts an adaptive processing of the second adaptive filter (202b) at a first time point partway through a second interval in which the first adaptive filter (202a) is continuously carrying out adaptive processing, where the second interval occurs in the first interval, and switches from the first adaptive filter (202a) to the second adaptive filter (202b) at a second time point, which is a time point after the first time point and which is the end point of the second interval.

8 Claims, 9 Drawing Sheets

(EXAMPLE OF DETERMINING INDICATIONS
OF FILTER DEGRADATION USING SN3)

$0.156718 - 0.117115 \approx 0.0396 < 0.04$

| HISTORY (SECONDS) | PRE-FILTERING SN3 | POST-FILTERING SN3 |
|---|---|---|
| 60 (OLDEST) | 0.124210 | 0.184473 |
| 56 | 0.068568 | 0.118469 |
| 52 | 0.065873 | 0.111315 |
| 48 | 0.059216 | 0.104766 |
| 44 | 0.096202 | 0.148943 |
| 40 | 0.199818 | 0.209080 |
| 36 | 0.373617 | 0.357530 |
| 32 | 0.079359 | 0.152353 |
| 28 | 0.077831 | 0.146197 |
| 24 | 0.077598 | 0.146142 |
| 20 | 0.062731 | 0.111669 |
| 16 | 0.074557 | 0.109650 |
| 12 | 0.063565 | 0.105882 |
| 8 | 0.105109 | 0.120666 |
| 4 | 0.166139 | 0.190862 |
| 0 (CURRENT) | 0.179446 | 0.189490 |
| AVERAGE | 0.117115 | 0.156718 |

PULSE WAVE SIGNAL
AND FFT RESULTS

SN3=13.3%

FILTERED PULSE WAVE SIGNAL (WITHOUT
RECONSTRUCTION PROCESSING) AND FFT RESULTS

SN3=21.1%

FILTERED PULSE WAVE SIGNAL (WITH
FILTER SWITCHING) AND FFT RESULTS

PULSE DETECTOR

CROSS-REFERENCE TO RELATED APPLICATIONS

This application claims priority to Japanese Patent Application No. 2011-041490 filed on Feb. 28, 2011. The entire disclosure of Japanese Patent Application No. 2011-041490 is hereby incorporated herein by reference.

BACKGROUND

1. Technological Field

The present invention relates to a pulse detector and the like.

2. Background Technology

A pulse detector is a device for detecting a pulse originating from a human heartbeat, and is a device for removing as noise a signal component (body movement effect signal) generated by the effects of human body movements from a signal (pulse wave signal) received from a pulse wave sensor worn on, e.g., the arm, palm, finger, or the like to detect a signal (pulse signal) derived from a heartbeat.

A pulse wave sensor of a type that is worn on a human finger or wrist is disclosed in, e.g., Patent Document 1. Art for filtering out and removing a noise component included in the pulse wave signal outputted from the pulse wave sensor is disclosed in, e.g., Patent Document 2. In the art described in Patent Document 2, a band-pass filter that admits a signal with a frequency approximate to the frequency showing the pulsation at that point is selected from among a plurality of band-pass filters.

Japanese Laid-open Patent Publication No. 2005-198829 (Patent Document 1) and Japanese Laid-open Patent Publication No. 2007-54471 (Patent Document 2) are examples of the related art.

SUMMARY

Problems to Be Solved by the Invention

In the art described in Patent Document 1, the pulse wave sensor is worn on a human finger, palm, or wrist, or the like. The finger, palm, or wrist, or the like is a location on the body with a particularly large amount of movement. Therefore, there is a large amount of noise intermixed with the pulse wave signal outputted from the pulse wave sensor when the pulse wave sensor is worn in such locations. For example, when the wearer moves the hand or a location near the hand, a change occurs in a separate bloodstream independent of the bloodstream produced by a heartbeat, and noise becomes entrained with the signal sensed by the pulse wave sensor.

In another example, the wearer's hand strikes an object or another location of the body of the wearer himself, whereby a separate change occurs in the bloodstream independent of bloodstream fluctuation produced by a heartbeat. Noise becomes intermixed with the pulse wave sensor output signal because the pulse wave sensor senses the change in bloodstream.

A wrist-type pulse detector (a pulse detector of a type that is worn on the wrist of a human or the like) in particular requires sufficient noise countermeasures because the resulting pulse wave signal is weaker than a finger-type pulse detector (a pulse detector of a type that is worn on the finger of a human or the like).

For example, the ulna, the radius, and other bones, as well as tendons and muscle come together in the wrist, and the shape of the tendons and muscles varies considerably when the fingers, hand, wrist, and other parts are moved. Change in the bloodstream occurs at such times. When the flow of blood in the arteries and veins is observed, changes in the bloodstream due to a heartbeat appear more clearly in the arteries than in the veins, and the rhythm of the heartbeat is therefore more readily apparent in the pulse wave signal as well. The motion of the heartbeat is difficult to see in the venous bloodstream. However, there are few arterial blood vessels in the subcutaneous tissue (shallow areas) on the external side of the wrist. In other words, there are few arteries in the wrist and such arteries are often in deeper positions. Therefore, changes in the bloodstream due to external factors become dominant more readily than changes in the bloodstream produced by the heartbeat when an attempt is made to capture changes in the bloodstream using a pulse wave sensor. For this reason, there is a high possibility that changes in the bloodstream will become difficult to see due to wrist motion or when an impact occurs around the hand.

In the art described in Patent Document 2, a band-pass filter that admits a signal with a frequency approximate to the frequency showing the pulsation at that point is selected from among a plurality of band-pass filters. However, a large number of judgment processes must be carried out by, e.g., software in order to achieve such a process, and the processing load is unarguably increased and the time required for the processing is increased. This leads to an increase in the size and power consumption of the pulse detector. It is critical that effective noise countermeasures be taken while the processing load and power consumption of the device is reduced in order to realize a pulse detector about, e.g., the size of a wristwatch.

In accordance with at least one aspect of the invention, it is possible to realize a pulse detector that can, e.g., carry out effective noise countermeasures while the processing load of the device is reduced. For example, it is possible to improve specific performance of the pulse-presenting spectrum that expresses the pulse signal in a pulse detector of a type in which the pulse wave sensor is worn on the external side of the wrist (the location in contact with the back lid surface of a wristwatch), or in a location where a pulse signal is difficult to acquire.

Means Used to Solve the Above-Mentioned Problems (1) A first aspect of the pulse detector of the invention is a pulse detector for detecting a pulse signal that originates from a pulse of a subject, the pulse detector characterized in comprising: a pulse wave sensor for outputting a pulse wave signal in which are intermixed the pulse signal and a noise signal including a body movement noise signal originating in the body movement of the subject; a pulse wave signal filtering section having a first adaptive filter and a second adaptive filter for self-adaptively adjusting a frequency response characteristic, the first and second adaptive filters being filters for filtering the pulse wave signal, and an adaptive filter switching section for switching the adaptive filter to be used, where the switching occurs in a first interval in which the pulse wave sensor is continuously operating; and a pulse wave frequency analyzer for performing a frequency analysis process at predetermined time intervals on the basis of a filtered signal outputted from the pulse wave signal filtering section and identifying a pulse-presenting spectrum that shows the pulse signal, wherein at a first time point partway through a second interval in which the first adaptive filter is continuously carrying out adaptive processing, where the second interval occurs in the first interval, the adaptive filter switching section causes the second adaptive filter to start adaptive processing, and switches from the first adaptive filter to the second adaptive filter at a second time point that is a time point after the first time point and is the end point of the second interval.

The adaptive filters are filters that can self-adaptively vary a transfer function on the basis of an input signal, i.e., filters that can self-adaptively adjust the frequency response characteristics. Adaptive filters are generally packaged as digital filters for carrying out digital signal processing. A predetermined algorithm (e.g., an optimization algorithm) is used in order to maintain a desired performance of the filters (e.g., the performance for minimizing the noise component included in an input signal). A signal obtained on the basis of a filtered signal is fed back to the predetermined algorithm, filter coefficients are adaptively varied by an adaptive process performed by the algorithm, and as a result, the frequency response characteristics of the adaptive filters can be varied. In the interval in which adaptive filter is continuously operating, the adaptive processing performed by the algorithm is continuously (intermittently) carried out, and the desired performance of the adaptive filter is maintained. The adaptive filters can be configured as filters for obtaining an output signal having high autocorrelation such as in, e.g., an adaptive line enhancer. In the case that a sudden fluctuation component has become intermixed with the pulse wave signal, the fluctuation component can be removed thereby.

However, when the adaptive filters operate continuously over a certain time period, the performance of the adaptive filter can fall below a desired level. This is due to the fact that a pulse signal (constant component) and a noise signal (non-constant component) that is included in the body movement noise signal, which originates in the body movement of the subject, are intermixed in the pulse wave signal outputted from the pulse wave sensor. In other words, the performance of the adaptive filters follows and varies with the pulse signal (constant component), but there is conversely a possibility that the performance will follow the noise signal as well. The level (signal amplitude) of the pulse signal and noise component fluctuate together with the passage of time, and can also fluctuate, e.g., suddenly and in a non-constant fashion. Therefore, the performance of the adaptive filters follows and varies with the noise component in the case that, e.g., the level of the pulse component is suddenly reduced and, at the same time, the level of the noise component is increased. The adaptive filters essentially select and output a signal with high autocorrelation from among the input signals; therefore, their performance progressively follows the noise in small increments together with the passage of time, and the filters gradually begin to allow the passage of noise signals. In this case, the performance of the adaptive filters is considerably reduced and it is sometimes difficult to restore a normal state when a certain amount of time has elapsed.

For example, a wristwatch-type pulse detector is worn on the wrist of the subject, and is continuously used over a long period of time in order to, e.g., record variation in the state of activity of the subject over time. Therefore, the performance of the adaptive filters is preferably not reduced with continuous use over a long period of time.

In view of the above, in the present aspect, a first adaptive filter and a second adaptive filter are provided, and an adaptive filter switching section switches with suitable timing the adaptive filter to be used.

If the state of the adaptive filter that is used after switching is a state in which suitable filter coefficients have been set, the performance of the post-switching adaptive filter will be better than the performance of the pre-switching adaptive filter, and suitable adaptive processing can therefore be maintained.

However, merely switching the adaptive filter does not necessarily mean that adaptive filter performance can be reliably maintained. For example, it is possible that the adaptive filter used immediately after the switch is performed will be in an initialized state (the filter coefficients have been set to all zero). In this case, it tends to be difficult for all frequency band signals to pass during an interval until adaptive processing (processing for updating the filter coefficients) is able to progress to a certain extent.

When a body movement noise component signal having a larger signal value than the pulse component signal becomes intermixed at this time, there is an unarguable possibility that the adaptive filters will adapt to the body movement noise component. In other words, there are cases in which adaptive processing progresses most rapidly in relation to the most dominant component signal in the pulse wave signal at the time that the filter coefficients were initialized. That is to say, there are cases in which it is difficult to obtain advantageous filter processing results for identifying the pulse-presenting spectrum (the frequency spectrum showing the period and signal strength of the pulse) when the external noise component signal is dominant immediately after the adaptive filters have been switched (at the time that the filter is initialized).

In consideration of this point, in the present aspect, adaptive processing of the next filter to be used is started prior to switching the adaptive filters, and the adaptive filters are switched at the point that adaptive processing has progressed to a certain extent. In this case, the post-switching adaptive filter is in a state of following a constant component (i.e., a pulse signal component having high correlation) included in the pulse wave signal, and it therefore becomes difficult to block the pulse component even if a non-constant noise is generated immediately after switching.

In other words, switching to an adaptive filter that has carried out a certain amount of adaptive processing in advance reduces the possibility of erroneously detecting the pulse-presenting spectrum in the case that frequency analysis is carried out using a fast Fourier transform (FFT) or the like.

In the present aspect, the use of a plurality of band-pass filters is not required because adaptive filters are used. The switching of the adaptive filters can be implemented by, e.g., switching sets of filter coefficients in software. Therefore, an increase in the processing load of the device is low, and an increase in the power consumption of the device is not particularly a problem.

Therefore, in accordance with the present aspect, it is possible to realize a pulse detector that can, e.g., carry out effective noise countermeasures while the processing load of the device (e.g., a pulse detector that can withstand long-term use) is reduced. For example, it is possible to improve specific performance of the pulse-presenting spectrum in a pulse detector of a type in which the pulse wave sensor is worn on the external side of the wrist (the location in contact with the rear cover surface of a wristwatch), or in a location where a pulse signal is difficult to acquire.

(2) In another aspect of the pulse detector of the invention, when the adaptive processing of the second adaptive filter is started, the adaptive filter switching section starts the adaptive processing from a state in which a filter coefficient has been initialized, or a state in which the filter coefficient has been set to a filter coefficient value of a time point in an interval in which the second adaptive filter had been operating continuously in the past.

In the present aspect, it is apparent that the adaptive processing of the adaptive filter that is used after switching adaptive filters is started in a state in which filter coefficients have been initialized, or in a state in which the filter coefficients have been set to filter coefficient values of a time point in an interval in which the post-switching adaptive filter had been operating continuously in the past. The state in which the filter coefficients have been initialized is a state in which, e.g., the filter coefficient values are all zero. When the filter begins adaptive processing from an initialized state and a certain amount of time has elapsed, the adaptive filters are in a state of being capable of following the pulse component and the adaptive filters can be switched at that time point.

The filter coefficient values of a time point in an interval in which the post-switching adaptive filter had been operating continuously in the past are preferred filter coefficient values obtained, e.g., when the adaptive filter that is used after switching had been operating continuously in the past. With this configuration, it is possible to anticipate an effect in which, e.g., the time of preliminary adaptive processing (a priori adaptive processing prior to switching adaptive filters) is reduced. In other words, the time for a priori adaptive processing can be shortened because the adaptation of the adaptive filter progresses and arrives more quickly at a preferred state.

(3) In another aspect of the pulse detector of the invention, the adaptive filter switching section has an adaptive filter performance evaluation section for evaluating the performance of the first adaptive filter; and the first time point is a time point at which the performance of the first adaptive filter is evaluated to have degraded by the adaptive filter performance evaluation section.

The adaptive filters are not required to be switched in the case that the performance of the in-service adaptive filter is high. In other words, the need to switch the adaptive filters occurs after indications of reduced performance of the in-service adaptive filter have appeared.

In view of this situation, in the present aspect, an adaptive filter performance evaluation section is provided, the performance degradation of the in-service adaptive filter is evaluated, and the adaptive processing of the next adaptive filter to be used is started (a priori adaptive processing) from the time point at which the in-service adaptive filter has been evaluated to be degraded.

(4) In another aspect of the pulse detector of the invention, the adaptive filter performance evaluation section evaluates the performance of the first adaptive filter on the basis of an index calculated on the basis of a frequency spectrum of at least one signal among the pulse wave signal prior to filtering by the pulse wave signal filtering section and the filtered signal outputted from the pulse wave signal filtering section.

In the present aspect, it is made apparent that an index calculated on the basis of a frequency spectrum of at least one signal among the pulse wave signal prior to filtering and the filtered signal outputted from the pulse wave signal filtering section is used in order to evaluate filter performance.

The performance of the adaptive filter can be determined on the basis of the distribution of the frequency spectrum, the peak value of the main baseline, or another parameter. Therefore, the index is calculated from the frequency analysis results of at least one of the pre-filtering signal or the filtered signal, and indications of degradation of filter performance can be determined on the basis of the value of the index.

(5) In another aspect of the pulse detector of the invention, the index is an index obtained by using the total value of the frequency spectrum appearing in the entire observed frequency band to divide the total of the value of the pulse-presenting spectrum and the value for each of the left and right spectra appearing adjacent to the pulse-presenting spectrum on the frequency axis; and the adaptive filter performance evaluation section evaluates the performance of the first adaptive filter by comparing a first value of the index obtained on the basis of the pulse wave signal before filtering by the pulse wave signal filtering section, and a second value of the index obtained on the basis of the filtered signal outputted from the pulse wave signal filtering section.

Indications of degradation of filter performance can be determined by finding the ratio of the spectrum values of the high-correlation signal component (pulse component) that is being extracted in relation to the total of all spectrum values in the observed frequency band.

In the present aspect, indications of degradation of adaptive filter performance are determined by using an index obtained by dividing the total of the spectrum values of the pulse-presenting spectrum and a single value each of the left and right spectrum values that appear adjacent to the pulse-presenting spectrum on the frequency axis by the total value of the frequency spectrum that appears in the entire observed frequency band; and then comparing the value (first value) of the index of the pre-filtering signal, and the value (second value) of the index of the filtered signal.

For example, if the filtering process is being properly carried out, the value (differential value) obtained by subtracting the second value from the first value is equal to or greater than a predetermined threshold value. A differential value that is less than the threshold value means that there is little difference between the state of the spectrum of the filtered signal and the state of the spectrum of the pre-filtering signal, and in this case, the performance of the adaptive filter can be evaluated as being degraded.

(6) In another aspect of the pulse detector of the invention, the second time point is a time point at which a predetermined time has elapsed from the first time point.

In the present aspect, the adaptive filters are switched at a time point at which a predetermined time has elapsed from the start of a priori adaptive processing of the next adaptive filter to be used. When a certain amount of time elapses after the start of a priori adaptive processing, the adaptation of the adaptive filter to be used after switching progresses to a certain extent, and preparation for adaptive filter switching can be viewed to be completed. The interval in which the next adaptive filter to be used is carrying out a priori adaptive processing is an interval in which the first adaptive filter and the second adaptive filter are both operating, and wasteful power consumption therefore increases when the interval is longer than necessary. Therefore, the adaptive filters are switched at a time point where a predetermined interval has elapsed for preparing for the adaptive filter switch.

(7) In another aspect of the pulse detector of the invention, the second time point is a time point at which a predetermined permissible time has elapsed from a third time point, which is the time point at which the second interval started.

In the present aspect, the time point (adaptive filter switching timing) at which the adaptive filters are switched is decided based on the starting point of continuous operation of the adaptive filter currently being used.

For example, when the predetermined permissible time has elapsed after the adaptive filter currently being used has started continuous operation, the adaptive filter can be switched regardless of, e.g., the existence of indications of degradation of the adaptive filter, whether the required time for a priori adaptive processing has elapsed, or other factors. In this case, the adaptive filters are switched when the cumulative service time of the in-service adaptive filter has reached a predetermined permissible time. Therefore, the adaptive filters can be reliably switched before the performance of the adaptive filter considerably degrades. Also, in accordance with the present aspect, the adaptive filters can be reliably switched even when, e.g., the indications of degradation of the adaptive filter have been overlooked for an unknown reason. Therefore, a situation does not occur in which the time that an adaptive filter has been continuously used without being switched extends beyond a permissible time.

(8) In another aspect of the pulse detector of the invention, the pulse wave signal filtering section comprises a delay processor for delaying the pulse wave signal by a predetermined time, a filter coefficient update section for updating the coefficient of at least one of the first adaptive filter and the second adaptive filter, and a subtractor; at least one of the first adaptive filter and the second adaptive filter selects and outputs a first signal having high autocorrelation from among the output signals of the delay processor; the subtractor subtracts the first signal from the pulse wave signal, generates a second signal having lower autocorrelation than the first signal, and feeds the second signal to the filter coefficient update section; and the filter coefficient update section updates the coefficient of at least one of the first adaptive filter and the second adaptive filter so that the second signal is suppressed.

In the present aspect, the pulse wave signal filtering section has a delay processor, adaptive filters, a filter coefficient update section, and a subtractor. The portion having these configurations can be referred to as an adaptive line enhancer. The filter coefficient update section updates the filter coefficients so that the second signal (a signal having low correlation and sometimes referred to as an error signal) outputted from the subtractor is suppressed (e.g., so as to be minimized).

In accordance with the present aspect, the adaptive filters can be switched with suitable timing. Therefore, the performance of the adaptive filters can be kept at a suitable level even in the case of long periods of continuous measurement. It is thereby possible to reduce the occurrence pulse detection failures and detection errors.

In this manner, in accordance with at least one aspect of the invention described above, the adaptive filters constituting the pulse wave signal filtering section are switched, e.g., with suitable timing, whereby it is possible to keep the performance of the adaptive filters at a suitable level. Since the adaptive filters are effectively used, the filter configuration can be simplified and the adaptive filters can be switched with relative ease. It is therefore possible to realize a pulse detector that can carry out effective noise countermeasures while the processing load of the device is reduced.

BRIEF DESCRIPTION OF THE DRAWINGS

Referring now to the attached drawings which form a part of this original disclosure:

FIG. 7 is a view showing an example of judging filter degradation indications using SN3 (S/N index);

DETAILED DESCRIPTION OF EXEMPLARY EMBODIMENTS

The invention is described in detail below with reference to the drawings. The present embodiment described below shall not be unreasonably limited to the details of the invention described in the claims. All of the aspects described in regard to the preferred embodiment are not necessarily the essential constituent features of the invention.

First embodiment

Overall Configuration Example

Figure 1:
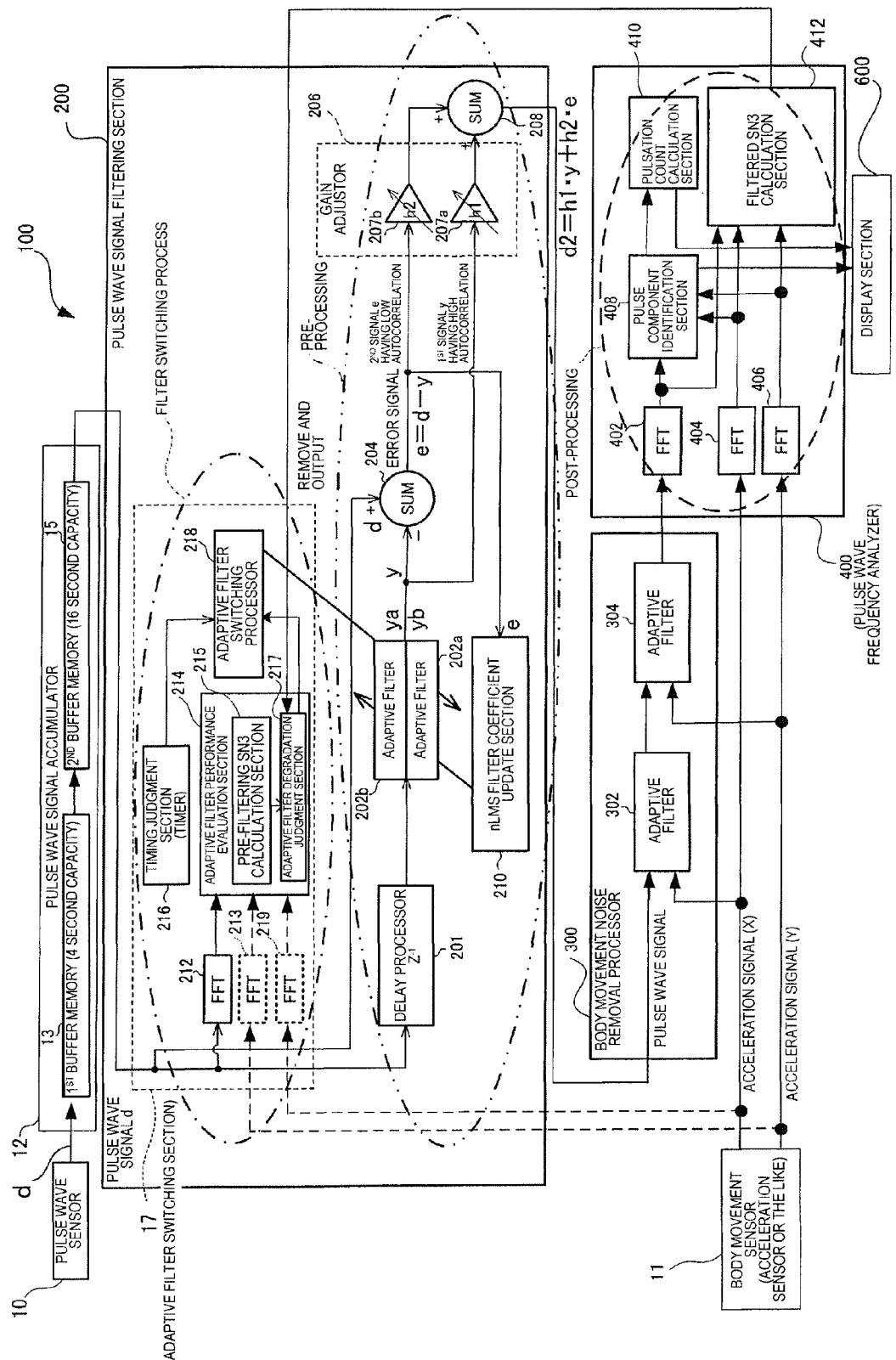
FIG. 1 is a view showing the configuration of an example of the pulse detector of the invention.

FIG. 1 is a view showing the configuration of an example of the pulse detector of the invention. The pulse detector 100 shown in FIG. 1 is a type of sensor device for detecting a pulse signal originating in the pulse of a subject (including humans and animals), as well as a heartbeat, and other biological information or the like that correspond to a pulse signal.

Here, the word "pulse" in a medical context refers to activity that occurs when periodic contractions and relaxations of the heart as well as internal organs in general are repeated. As used herein, the term "pulse" refers to pumping motion in which the heart periodically sends blood. A heartbeat count is referred to as the number of pulses of the heart in a single minute. The pulsation count is the number of pulsatory motions in a peripheral blood vessel. This number of times thus counted shall be referred to as a "pulsation count" or merely as a "pulsation" because pulsatory motions occur in the arteries when the heart sends blood out. When measuring the pulse in the arm, it is common in medical parlance to refer to it as the pulsation count rather than heartbeat count. Also, in the description below, the term "body movement" is used. Constant (periodic) body movement of the subject can be narrowly-defined body movement. For example, the constant periodic motion of the arm (the vicinity of the location where the pulse rate meter is worn) that accompanies, e.g., walking, jogging, or the like corresponds to a narrow definition of body movement.

The pulse detector 100 shown in FIG. 1 has a pulse wave sensor 10; a pulse wave signal accumulator (having a first buffer memory 13 for accumulating four seconds of pulse wave signal d data, and a second buffer memory 15 for accumulating 16 seconds of pulse wave signal d data) 12; a pulse wave signal filtering section 200 that includes an adaptive filter switching section 17; a body movement sensor (an acceleration sensor, gyro sensor, or the like) 11; a body movement noise removal processor 300; a pulse wave frequency analyzer 400; and a display section (including a liquid crystal panel or the like) 600 for displaying detection results and the like.

The pulse wave sensor 10 is a pulse wave sensor based on, e.g., a photoelectric pulse wave sensor and the principles thereof. The pulse wave sensor 10 outputs the pulse wave signal d in which a pulse signal and a noise signal that includes body movement noise signals which originate in the body movement of the subject (human or animal).

As used herein, the pulse wave signal d includes, e.g., a pulse component signal (a constant component or a periodic component), a body movement noise component (a constant or periodic component), and an external noise component (impact noise or other non-constant or aperiodic component).

A four-second duration of the pulse wave signal d outputted from the pulse wave sensor 10 is accumulated in the first buffer memory 13. The four-second pulse wave signal d is transferred to the second buffer memory 15 in four-second cycles. The second buffer memory 15 is first-in, first-out (FIFO) memory, and 16 seconds of the pulse wave signal is updated in four-second segments. The reason that 16 seconds of the pulse wave signal is accumulated is that changes in the signal must be observed for a certain length of time to carefully evaluate the existence of a correlation or other parameter when the pulse component is to be identified by frequency analysis.

The pulse wave signal filtering section 200 is a type of adaptive filter that can separate and output a constant frequency component and other aperiodic components when such components are included in the input signal.

The pulse wave signal filtering section 200 has a delay processor 201 for delaying the pulse wave signal for a predetermined time (a single sample time in this case); a first adaptive filter 202a and a second adaptive filter 202b that select and output a first signal y having the highest autocorrelation from among the output signals of the delay processor 201, either of the adaptive filters being used in a selective fashion; a filter coefficient update section (nLMS filter coefficient update section) 210 for updating the coefficients of the adaptive filters 202a, 202b; and a subtractor 204 for subtracting a first signal y (i.e., ya, yb) from the pulse wave signal d, generating a second signal e (=d−y:ea=d−ya or eb=d−yb) having lower autocorrelation than the first signal y (ya, yb), and feeding (feedback) the second signal e to the filter coefficient update section (nLMS filter coefficient update section) 210.

A functional block that includes the delay processor 201, the first adaptive filter 202a, the second adaptive filter 202b, and the filter coefficient update section (nLMS filter coefficient update section) 210 is sometimes referred to as an adaptive line enhancer. An adaptive line enhancer is an adaptive filter (or adaptive filter section) having a function for separating and outputting, e.g., a constant frequency component (a component with high correlation), and other non-constant components (components with low correlation) when such components are included.

The filter coefficient update section (nLMS filter coefficient update section) 210 adaptively updates the coefficients (in this case, the normalized least mean square coefficients (nLMS coefficients)) of the adaptive filters so that the value of the second signal e is controlled (e.g., minimized). The filter coefficients are updated independently for each adaptive filter 202a, 202b. In other words, a first signal ya is outputted from the first adaptive filter 202a and a first signal yb is outputted from the second adaptive filter 202b. The subtractor 204 calculates a second signal ea by subtracting the first signal ya from the pulse wave signal d (=d−ya), and calculates a second signal eb by subtracting the first signal yb from the pulse wave signal d (=d−yb). The filter coefficients of the first adaptive filter 202a are updated on the basis of the second signal ea. The filter coefficients of the second adaptive filter 202b are updated on the basis of the second signal eb.

For the sake of description, the first signal from the in-service adaptive filter will be merely denoted as y, and the second signal will be merely denoted as e. The same denotation is used in FIG. 1 as well in relation to the input and output signals of the subtractor 204.

The first signal y and the second signal e (−d−y) are multiplied by gain coefficients h1, h2 (this process is carried out by coefficient multipliers 207a, 207b included in a gain adjustor 206), and the two signals are thereafter added together by an adder 208. For example, h1≥1.0 and h2<1.0. In accordance therewith, the effect of an impact is reduced and the ability to follow rapid changes in the pulse and body movement components can be increased. For example, it is possible that the adaptive filters 202 will block the signal of the heartbeat component during a rapid increase when a person having a pulse of 60 at rest begins jogging at a high pace and the pulse rapidly increases to 150 and the following ability of the adaptive filter 202 is slower than the increase in the pulse. This situation can be avoided.

The first adaptive filter 202a and the second adaptive filter 202b (these can be referred to as adaptive filters in the description below) can self-adaptively change the transfer functions on the basis of the input signal, i.e., are capable of self-adaptively adjusting the frequency response characteristics.

The first adaptive filter 202a and the second adaptive filter 202b are generally packaged as digital filters for carrying out digital signal processing. A predetermined algorithm (e.g., an optimization algorithm) is used in order to maintain a desired performance of the adaptive filters (e.g., the performance for minimizing the noise component included in the input signal). A signal obtained on the basis of a filtered signal is fed back to the predetermined algorithm, the filter coefficients are adaptively varied by an adaptive process performed by the algorithm, and as a result, the frequency response characteristics of the adaptive filters can be varied.

In the interval in which the pulse wave sensor 10 is continuously operating (i.e., the interval in which the sampled pulse wave signal d is continuously being outputted), the adaptive processing performed by the algorithm is continuously (intermittently) carried out, and the desired performance of the first adaptive filter 202a or the second adaptive filter 202b is maintained.

However, when either of the adaptive filters operates continuously over a certain time period, the performance of the adaptive filter can fall below a desired level. This is due to the fact that a pulse signal (constant component) and a noise signal (non-constant component) that is included in the body movement noise signal, which originates in the body movement of the subject, are intermixed in the pulse wave signal d outputted from the pulse wave sensor 10. In other words, the performance of the adaptive filters 202 follows and varies with the pulse signal (constant component), but there is conversely a possibility that the performance will follow the noise signal as well. The level (signal amplitude) of the pulse signal and noise component fluctuate together with the passage of time, and can also fluctuate, e.g., suddenly or in a non-constant fashion. Therefore, the performance of the adaptive filters 202 follows and varies with the noise component in the case that the level of the pulse component is suddenly reduced and at the same time the level of the noise component is increased. The adaptive filters 202 essentially select and output a signal with high autocorrelation from among the input signals and therefore progressively follow the noise in small increments together with the passage of time and gradually also begin to allow the passage of noise signals. In this case, the performance of the in-service adaptive filter is considerably reduced and it is sometimes difficult to restore a normal state when a certain amount of time has elapsed.

In view of the above, in the present embodiment, the adaptive filter switching section 17 carries out processing with suitable timing to switch from the in-service adaptive filter to the other adaptive filter among the first adaptive filter 202a and the second adaptive filter 202b (adaptive filter switching processing).

If the state of the adaptive filter that is used after switching is a state in which suitable filter coefficients have been set, the performance of the post-switching adaptive filter will be better than the performance of the pre-switching adaptive filter, and suitable adaptive processing can therefore be maintained.

However, merely switching the adaptive filter does not necessarily mean that adaptive filter performance can be reliably maintained. For example, consider the case in which the post-switching adaptive filter immediately after switching has been initialized (the filter coefficients have been set to all zeros). In this case, it tends to be difficult for all frequency band signals to pass during an interval until adaptive processing (processing for updating the filter coefficients) can progress to a certain extent.

When a body movement noise component signal having a larger signal value than the pulse component signal becomes intermixed at this time, there is an unarguable possibility that the adaptive filters will adapt to the body movement noise component. In other words, there are cases in which adaptive processing progresses most rapidly in relation to the most dominant component signal in the pulse wave signal at the time that the filter coefficients have been initialized. That is to say, there are cases in which it is difficult to obtain advantageous filter processing results for identifying the pulse-presenting spectrum when the external noise component signal is dominant immediately after the adaptive filters have been switched (at the time that the filter is initialized).

In consideration of this point, in the present embodiment, adaptive processing of the next filter to be used is started prior to switching the adaptive filters, and the adaptive filters are switched at the point that adaptive processing has progressed to a certain extent.

In other words, at a first time point partway through a second interval in which one of the adaptive filters among the first adaptive filter 202a and the second adaptive filter 202b is continuously carrying out adaptive processing, the adaptive filter switching section 17 causes the other adaptive filter to start adaptive processing, the second interval occurring in a first interval in which the pulse wave sensor 10 is continuously operating. The adaptive filter to be used is switched at a second time point, which is a time point after the first time point and which is the end point of the second interval.

At the time point (first time point) at which the adaptive processing of the other adaptive filter is to be started, the other adaptive filter is preferably in a state in which the filter coefficients have been initialized or in a state in which the filter coefficients have been set to filter coefficient values of a time point in an interval in which the other adaptive filter had been continuously operating. In this case, the state in which the filter coefficients have been initialized is a state in which, e.g., the filter coefficient values are all zero. When the filter begins adaptive processing from an initialized state and a certain amount of time has elapsed, the adaptive filters are in a state of being capable of following the pulse component and the adaptive filters can be switched at that time point (second time point).

The filter coefficient values of a time point in an interval in which the post-switching adaptive filter had been operating continuously in the past are preferred filter coefficient values obtained, e.g., when the adaptive filter that is used after switching had been operating continuously in the past. With this configuration, it is possible to anticipate an effect in which, e.g., the time of preliminary adaptive processing (a priori adaptive processing prior to switching adaptive filters) is reduced. In other words, the time for a priori adaptive processing can be shortened because the adaptation of the adaptive filter progresses and arrives more quickly at a preferred state. In other words, the timing at which the second time point arrives can be made sooner. The details of processing for switching the adaptive filters are described below.

The post-switching adaptive filter is in a state of having been operating over a certain period of time at the switching time point (i.e., a priori adaptive processing is in progress), and is in a state of following a constant component (i.e., a pulse signal component having high correlation) included in the pulse wave signal d. Therefore, it becomes difficult to block the pulse component even if a non-constant noise is generated immediately after switching.

In other words, switching to an adaptive filter whereby a certain amount of adaptive processing has been performed in advance reduces the possibility of erroneously detecting the pulse-presenting spectrum that expresses the pulse (a frequency spectrum showing the period and signal strength of the pulse) in the case that frequency analysis is carried out using fast Fourier transform (FFT) or the like.

As shown in FIG. 1, the adaptive filter switching section 17 preferably has a fast Fourier transform section 212 for carrying out a fast Fourier transform (FFT); fast Fourier transform sections 213, 219 that can be provided as needed; an adaptive filter performance evaluation section 214; a timing determination section (timer) 216; and an adaptive filter switching processor 218. The timing determination section (timer) 216 measures the elapsed time using, e.g., the measurement start time point as a reference, and manages the switching timing of the adaptive filters.

The fast Fourier transform section 212 performs a fast Fourier transform on the pulse wave signal d. In the case that the fast Fourier transform sections 213, 219 are provided, the fast Fourier transform section 213 performs a fast Fourier transform on the acceleration signal (X-direction component) outputted from the body movement sensor 11, and the fast Fourier transform section 219 performs a fast Fourier transform on the acceleration signal (Y-direction component) outputted from the body movement sensor 11.

The adaptive filter performance evaluation section 214 has a pre-filtering SN3 calculation section 215, an adaptive filter degradation determination section 217, and an adaptive filter switching processor 218.

The adaptive filters are not required to be switched in the case that the performance of the in-service adaptive filter is high. In other words, the need to switch the adaptive filters occurs after indications of reduced performance of the in-service adaptive filter have appeared.

In view of this situation, in the present embodiment, the adaptive filter performance evaluation section 214 is provided, indications of performance degradation of the in-service adaptive filter are detected, and the adaptive processing of the next adaptive filter to be used is started (a priori adaptive processing) from the detection time point.

An index related to the performance of the adaptive filters is required in order to objectively evaluate the performance of the adaptive filters. In the present embodiment, there is used an S/N index (e.g., an index referred to as SN3) that is calculated on the basis of at least one signal among the frequency spectrum of the pre-filtering pulse wave signal d or the filtered signal (including the signal from which body movement noise has been removed) outputted from the pulse wave signal filtering section 200.

The performance of the adaptive filter is preferably determined on the basis of the distribution of the frequency spectrum, the peak value of the main baseline, or another parameter. Therefore, the index is calculated from the frequency analysis results of at least one of the pre-filtering signal or the filtered signal, and indications of degradation of filter performance can be determined on the basis of the value of the index.

Here, SN3 is an S/N index for evaluating the performance of the adaptive filters, and is an index obtained by using the total value of the frequency spectrum that appears in the entire observed frequency band to divide the total of the value of the pulse-presenting spectrum and the value for each of the left and right spectra appearing adjacent to the pulse-presenting spectrum on the frequency axis.

In other words, SN3 can be expressed in the following formula. SN3=(total value of the pulse-presenting spectrum and each of the spectra to the left and right of the pulse-presenting spectrum)/(total of the spectrum values in the entire frequency band 0 to 4 Hz) (units: %)
The pulse-presenting spectrum is a frequency spectrum that shows the period and signal strength of the pulse in the frequency spectrum obtained as the FFT result of the pulse component signal of a fixed interval.

In other words, SN3 is used as an index because an indication of degraded performance of the adaptive filters can be determined by finding the ratio of the spectrum values of the high-correlation signal component (pulse component) that is being extracted in relation to the total of all spectrum values in the observed frequency band.

For example, the pre-filtering SN3 calculation section 215 calculates the SN3 for the pre-filtering pulse wave signal d (original signal). A post-filtering SN3 calculation section 412 is provided to the pulse wave frequency analyzer 400, and the post-filtering SN3 calculation section 412 calculates the SN3 for the filtered signal (the filtered pulse wave signal).

For example, the index value (first value) for the pre-filtering signal that has been calculated by the pre-filtering SN3 calculation section 215, and the index value (second value) for the filtered signal that has been calculated by the post-filtering SN3 calculation section 412 are inputted to the adaptive filter degradation determination section 217 included in the adaptive filter performance evaluation section 214. The adaptive filter degradation determination section 217 compares the first and second values and determines the existence of indications of performance degradation of the in-service filter.

For example, if the filtering process is being properly carried out, the value (i.e., the differential value) obtained by subtracting the second value of SN3 from the first value of SN3 should be equal to or greater than a predetermined threshold value. A differential value that is less than the threshold value means that there is little difference between the state of the spectrum of the filtered signal and the state of the spectrum of the pre-filtering signal, and in this case, the adaptive filter is not working effectively and it is therefore determined that there are indications of performance degradation of the adaptive filter. In other words, at that time point, indications of performance degradation of the adaptive filter have been detected.

The evaluation of the performance of the adaptive filter can also be made on the basis of the first value or the second value of SN3 (either independently). In other words, the SN3 value increases if the performance of the adaptive filter is high, and the SN3 value decreases in accompaniment with a reduction the performance of the adaptive filter. Therefore, indications of filter performance degradation can be detected by, e.g., comparing the SN3 value and a predetermined threshold value. However, as described above, the precision of determining indications of performance degradation of the adaptive filter can be increased by using the method of comparing the first and second values of SN3.

In FIG. 1, the body movement sensor 11 is a sensor for detecting the constant periodic motion of the arm (the vicinity of the location where the pulse rate meter is worn) that accompanies the body movement, e.g., walking, jogging, or the like of the subject; and can include, e.g., an acceleration sensor or a gyro sensor.

The body movement noise removal processor 300 has a first adaptive filter 302 and second adaptive filter 304 for removing body movement noise. Body movement noise (the body movement noise component) is a noise component that is included in the pulse wave signal (more specifically, the output signal of the adder 208) and that shows variation in blood vessel capacity that is caused by constant activity and action (body movement) of a human. In the case of a pulse rate meter worn on the arm or finger, variation is generated in blood vessel capacity together with the rhythm of the swinging arm due to the effect of swinging the arm while walking or jogging. A human performs constant action, whereby a component signal having the frequency of the action is produced. The body movement noise component is known to have high correlation with the signal waveform outputted by an acceleration sensor worn in the vicinity of the location where the pulse wave sensor is worn.

The pulse wave frequency analyzer 400 has a fast Fourier transform section 402 that receives input of the pulse wave signal after body movement noise removal; a fast Fourier transform section 404 that receives input of the acceleration signal (X-axis direction component) from the body movement sensor 11; a fast Fourier transform section 406 that receives input of the acceleration signal (Y-axis direction component) from the body movement sensor 11; a pulse component identifier (pulse-presenting spectrum identifier) 408, and a pulsation count calculation section 410. As described above, the pulse wave frequency analyzer 400 can also have a post-filtering SN3 calculation section 412 as needed.

The pulse component identifier (pulse-presenting spectrum identifier) 408 performs a frequency analysis every four seconds for 16 seconds of the pulse wave signal after FFT, examines the correlation with past pulse components on the basis of the spectrum values, the spectrum distribution, and the like, and identifies the pulse-presenting spectrum. As described above, the pulse-presenting spectrum is a frequency spectrum that shows the period and signal strength of the pulse in the frequency spectrum obtained as a result of FFT of the pulse component signal for a fixed interval. The body movement presentation spectrum is a frequency spectrum that shows the period and signal strength of the body movement (e.g. arm swinging while walking) in the frequency spectrum obtained as a result of FFT of the body movement noise component signal for a fixed interval.

The pulsation count calculation section 410 calculates the pulsation count. Essentially, the pulsation count is unambiguously established in relation to the position of the spectrum as long as the position (frequency) of the pulse-presenting spectrum on the frequency axis is established.

As described above, the post-filtering SN3 calculation section 412 calculates the SN3 value (second value) for a filtered signal.

The waveform showing the detected pulsation count and pulse, the detected state of activity, the burned calories of the subject, the current time, and other information can be displayed on the display section 600.

In the pulse detector 100 shown in FIG. 1, the switching of the first adaptive filter 202a and the second adaptive filter 202b is carried out with suitable timing. Therefore, the switched-to filter can start adaptive processing from an advantageous adaptive state even if the filter performance has been reduced by continuous use of the adaptive filters 202 (e.g., even in the case that the pulse signal is not followed because following the noise signal has become dominant), and as a result, self-adaptation can efficiently progress so as to capture the pulse signal. Therefore, the filter performance is constantly kept in an advantageous state for following the pulse signal.

In the pulse detector 100 of FIG. 1, the use of a plurality of band-pass filters is not required because adaptive filters 202 are used, and there is furthermore no need to determine in accordance with predetermined conditions which band-pass filter output to use as the output signal. The adaptive filters can be switched in a simple manner, the increase in the processing load of the device is low, and an increase in the power consumption of the device is not particularly a problem.

Therefore, in accordance with the present embodiment, it is possible to realize a pulse detector 100 that can, e.g., carry out effective noise countermeasures while reducing the processing load of the device (e.g., a pulse detector 100 that can withstand long-term use). For example, it is possible to improve specific performance of the pulse-presenting spectrum in a pulse detector of a type in which the pulse wave sensor 10 is worn on the external side of the wrist (the location in contact with the back lid surface of a wristwatch), or in a location where a pulse signal is difficult to acquire.

Example of a Wristwatch-type Pulse Rate Meter

Figure 2A:
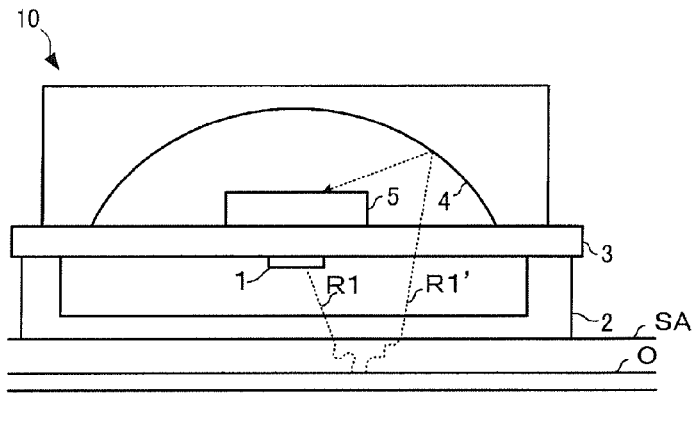
FIGS. 2A to 2C are views showing an example of the configuration of the pulse wave sensor and the pulse detector.
Figure 2B:
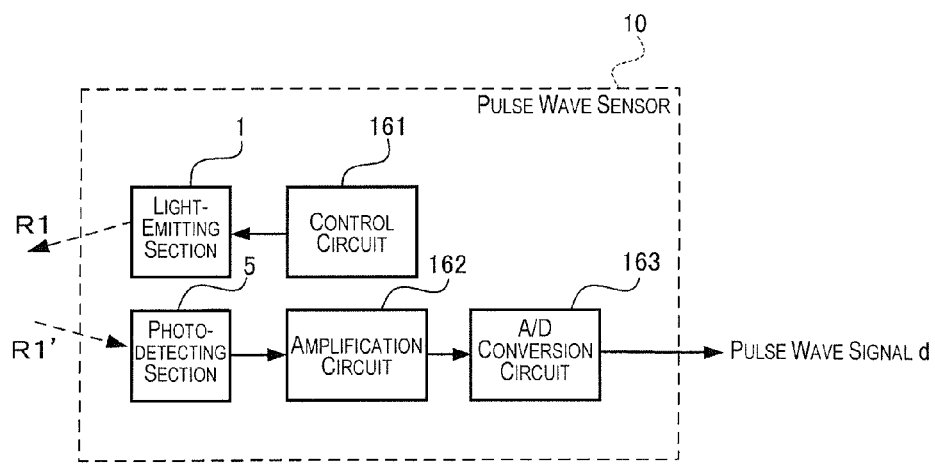
Figure 2C:
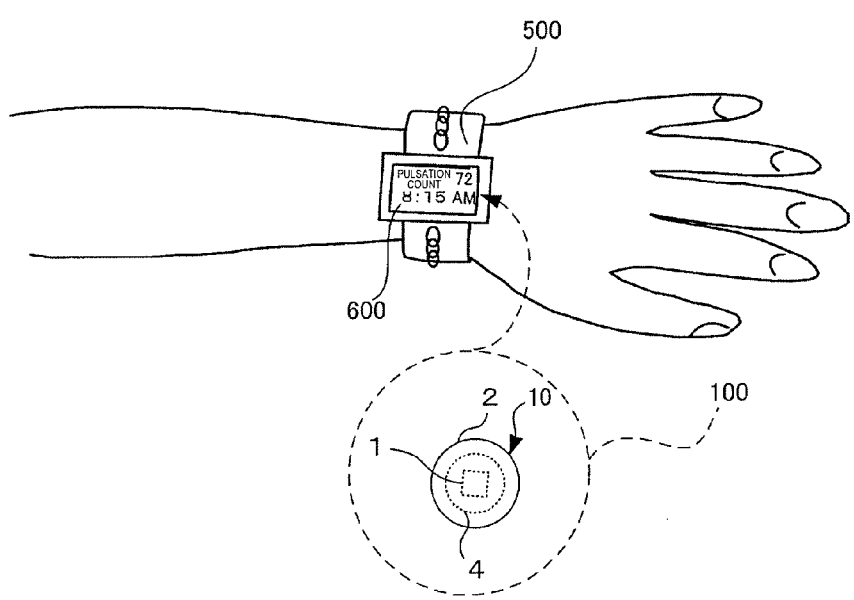

FIGS. 2A to 2C are views showing an example of the configuration of the pulse wave sensor and the pulse detector. FIG. 2A shows the cross-sectional structure of an example of the pulse wave sensor 10. The pulse wave sensor 10 shown in FIG. 2A has a light-emitting element 1 provided to the reverse surface (lower surface) of a substrate 3, a transparent cover (a contact member composed of a light-transmitting material) 2, a light-reflecting dome (light-reflecting section) 4, and a light-receiving section 5 provided to the obverse surface (upper surface) of the substrate 3. Light R1 emitted from the light-emitting element 1 arrives at and is reflected from a blood vessel (biological information source) O in a detection area SA (the wrist in this case). The strength of the reflected light R1' fluctuates in a periodic fashion in response to a pulse because the capacity of the blood vessel O fluctuates in periodic fashion in accompaniment with the pulse. The reflected light R1' is reflected by the light-reflecting dome 4 and is then incident on the light-receiving section 5. The light-receiving section 5 converts the incident light into an electric signal.

FIG. 2B shows an example of the circuit configuration in the pulse wave sensor 10. The light emission of the light-emitting element 1 is controlled by a control circuit 161. The light-receiving signal outputted from the light-receiving section 5 is amplified by an amplification circuit 162 and is thereafter converted into a digital signal by an A/D conversion circuit 163. The pulse wave signal d is obtained in this manner.

FIG. 2C shows a usage example of a wristwatch-type pulse rate meter (housing the pulse detector of the present embodiment). The pulse rate meter has a wristband 500, a display section 600, and the (housed) pulse detector 100 of the present embodiment. In the example of FIG. 2C, the pulse rate meter (i.e., the pulse detector 100) is worn on the left wrist of person (user) as the subject.

Process for Switching Adaptive Filters

Figure 3A:
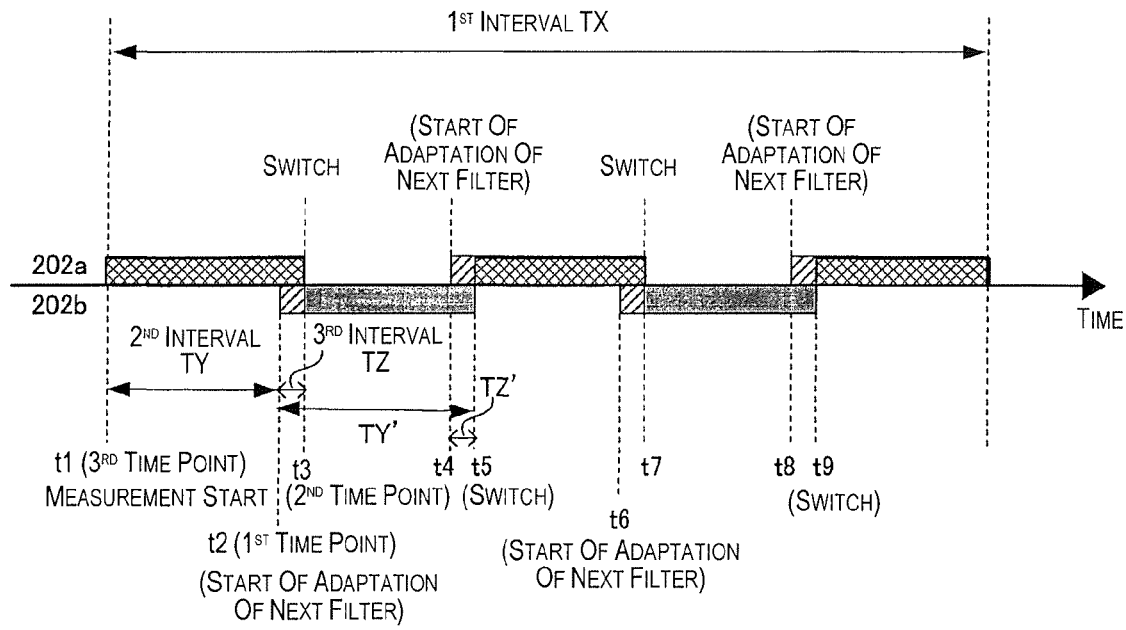
FIGS. 3A and 3B are views showing an example of the timing of the process for switching adaptive filters, and the configuration for switching filters.
Figure 3B:
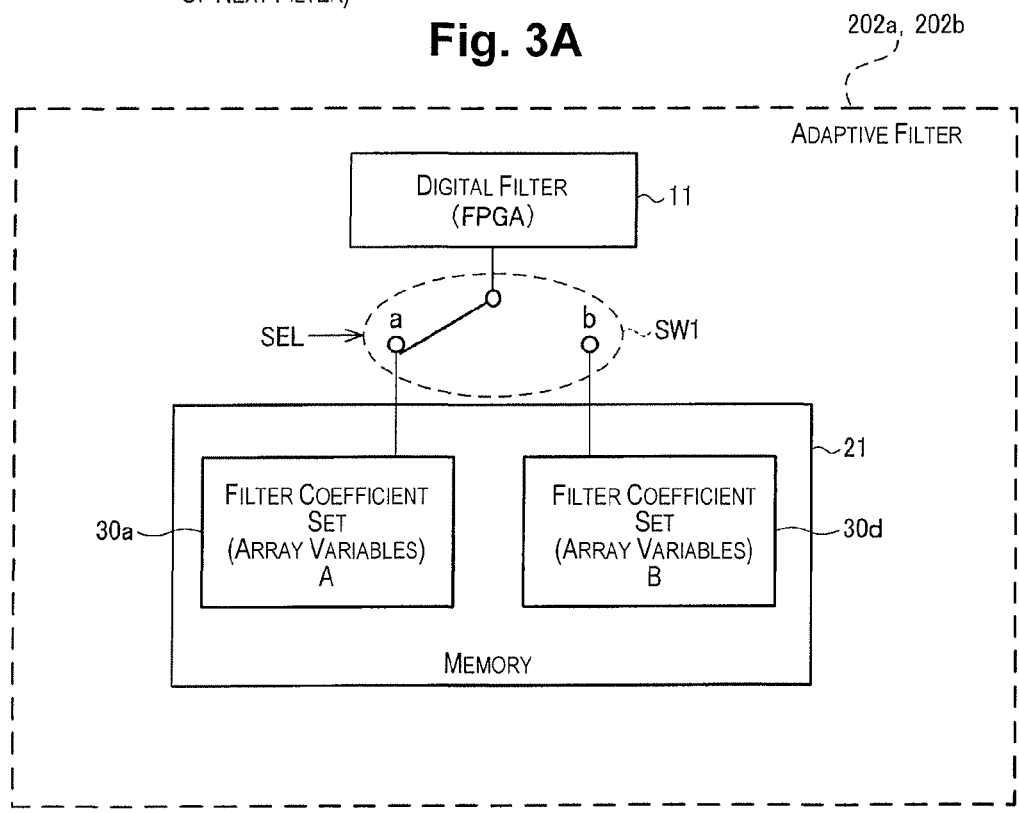

FIGS. 3A and 3B are views showing an example of the timing of the process for switching adaptive filters, and the configuration for switching filters.

FIG. 3A shows an example of the timing of the process for switching adaptive filters. The operating time of the first adaptive filter 202a is shown on the upper side of the time axis (the reticulated portion). The operating time of the second adaptive filter 202b is shown on the lower side of the time axis (the hatched portions and shaded portions).

The pulse detector 100 starts the pulse detection process (i.e., measurement process) at time t1 and the operation is continued until time t10. A first interval TX from time t1 to time t10 is an interval in which the pulse wave sensor 10 is continuously operating. In the first interval TX, a pulse wave signal is continuously outputted, and a pulse signal of the subject (the human body in this case) and a noise signal that includes a body movement noise signal originating in body movement are intermixed in the pulse wave signal.

The operation of the first adaptive filter 202a starts at time t1. The timing for switching to the next filter arrives at time t3. The first adaptive filter 202a continuously operates until time t3. The second adaptive filter 202b starts adaptive processing (a priori adaptive processing) at time t2, a predetermined time prior to time t3, which is the timing for switching the adaptive filters. A third interval TZ from time t2 to time t3 is an interval in which the second adaptive filter 202b carries out a priori adaptive processing.

The same operation is repeated hereinbelow. TY' is a second interval (next second interval) in which the second adaptive filter 202b is continuously operating; and TZ' is a third interval (next third interval) in which the first adaptive filter 202a is carrying out a priori adaptive processing.

The start timings (times t2, t4, t6, t8) of the adaptive processing of the next adaptive filter to operate can be time points at which indications of degradation in the in-service adaptive filter have been detected as described above.

The adaptive filters can be switched at time points (times t3, t5, t7, t9) at which a predetermined time has elapsed from the start of a priori adaptive processing by the next adaptive filter to be used (described as 'next filter' in FIG. 3). In other words, when a certain amount of time elapses after the start of a priori adaptive processing, the adaptation of the adaptive filter to be used after switching progresses to a certain extent, and preparation for adaptive filter switching can be viewed to be completed. The interval in which the next adaptive filter to be used is carrying out a priori adaptive processing is an interval in which the first adaptive filter 202a and the second adaptive filter 202b are both operating, and wasteful power consumption therefore increases when the interval is longer than necessary. Therefore, the adaptive filters are preferably switched at a time point where a predetermined interval has elapsed for preparing for the adaptive filter switch.

However, this is an example. The time point at which the adaptive filters are switched can be decided using, e.g., the starting time point of continuous operation of the adaptive filter that is currently in use as a reference. For example, when a predetermined time (a predetermined permissible time) has elapsed from the time point at which the adaptive filter that is currently in use stand continuous operation (times t1, t2, t4, t6, t8 in FIG. 3A), the adaptive filters can be switched regardless of, e.g., the existence of indications of degradation of the adaptive filter, whether the required time for a priori adaptive processing has elapsed, or other factors. This point is later described in detail.

FIG. 3B is a view showing an example of the configuration for switching the adaptive filters. The first adaptive filter 202a and the second adaptive filter 202b can be essentially composed of e.g., a digital filter (hardware) 11 composed of a field-programmable gate array (FPGA); a memory 21 for storing a filter coefficient set (array variables) A30a for the first adaptive filter 202a and a filter coefficient set (array variables) B30d for the second adaptive filter 202b; and a switch SW1 (which is switched by a switch control signal SEL) for switching the filter coefficient set (array variables) A and the filter coefficient set (array variables) B.

A state in which the switch SW1 has switched to an a terminal side is a state in which the first adaptive filter 202a is operating; and a state in which the switch SW1 has switched to an b terminal side is a state in which the second adaptive filter 202b is operating.

In the present embodiment, the use of a plurality of bandpass filters is not required because adaptive filters are used. The switching of the adaptive filters can be implemented by, e.g., switching sets of filter coefficients in software. Therefore, an increase in the processing load of the device is low, and an increase in the power consumption of the device is not particularly a problem.

Figure 4:
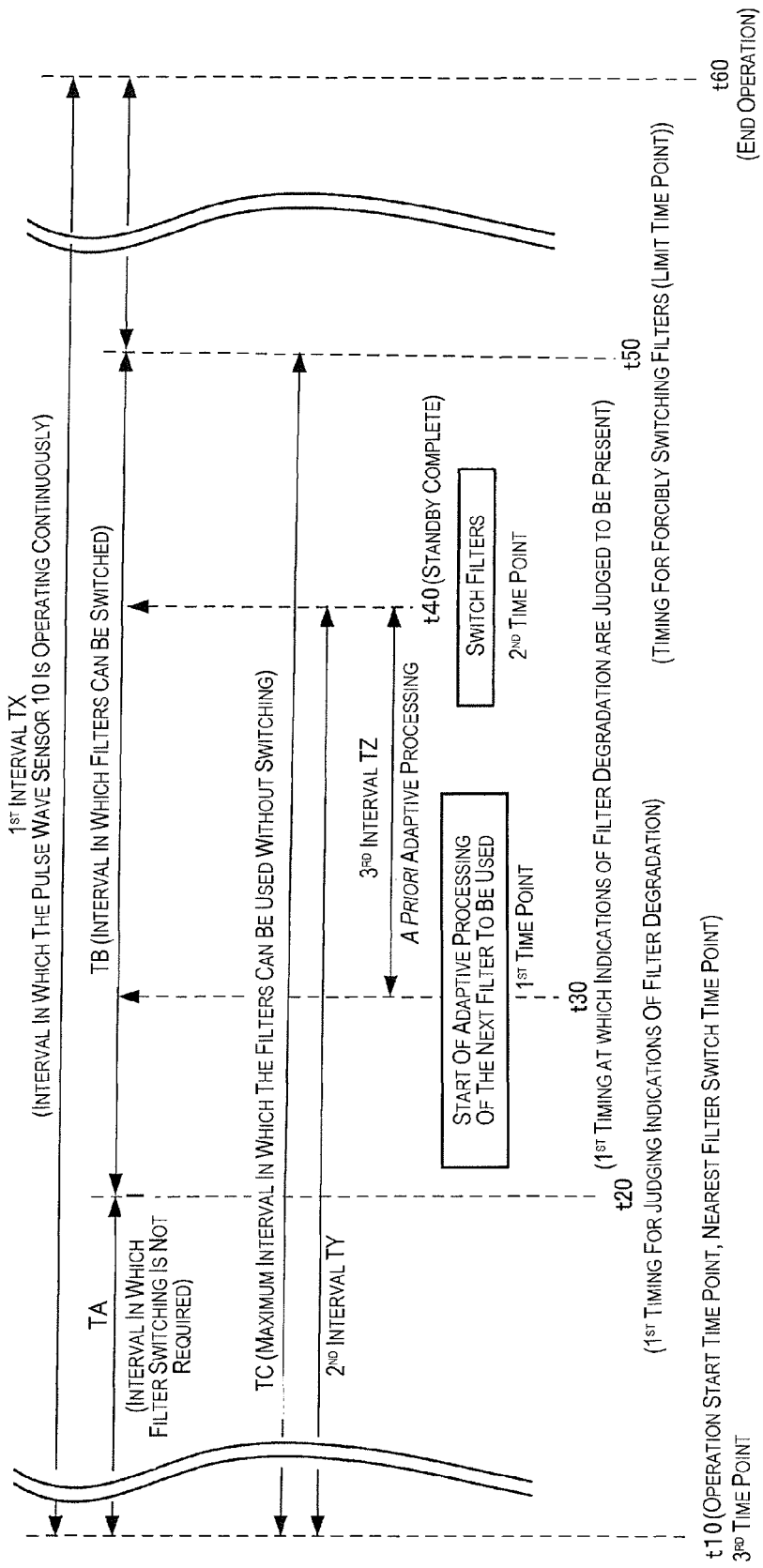
FIG. 4 is a timing chart showing a specific example of the timing of the filter-switching process.

A more specific example of the timing for switching the adaptive filters is described next. FIG. 4 is a timing chart showing a specific example of the timing of the process for switching adaptive filters.

In FIG. 4, the interval from time t10 to time t60 is the first interval TX in which the pulse wave sensor 10 is operating continuously. The time t10 to time t40 is a second interval (more exactly, the first second interval) TY in which the first adaptive filter 202a operates continuously. The time t30 to time t40 is a third interval (more exactly, the first third interval) in which the second adaptive filter 202b that is next to be used carries out a priori adaptive processing.

In FIG. 4, for example, the time point (time t10: third time point) at which the first adaptive filter 202a started operation to the time t20 at which the first time (e.g., 10 minutes) elapsed is an interval TA in which the first adaptive filter 202a is not required to be switched. The interval TA can be regularly set using the time t10 as a reference.

The time t20 to time t50 at which the second time (e.g., five minutes) elapsed is an interval TB in which the adaptive filters can be switched.

The time t50 is timing (limit time point) for forcibly switching the adaptive filters. The time t50 is a time point at which a predetermined permissible time has elapsed from the time t10 at which the first adaptive filter 202a, which is the currently operating adaptive filter, started continuous operation. In the present embodiment, the adaptive filters are switched at time t50 regardless of, e.g., the existence of indications of degradation of the adaptive filter, whether the required time for a priori adaptive processing has elapsed, or other factors.

In such a configuration, the adaptive filters are switched when the cumulative service time of the in-service adaptive filter (the first adaptive filter 202a in this case) has reached a predetermined permissible time. Therefore, the adaptive filters can be reliably switched before the performance of the adaptive filter considerably degrades. Also, the adaptive filters can be reliably switched even when, e.g., the indications of degradation of the adaptive filter have been overlooked for an unknown reason. Therefore, a situation does not occur in which the time that an adaptive filter has been continuously used without being switched extends beyond a permissible time.

An interval TC from time t10 to time t50 is the maximum interval in which the first adaptive filter 202a, which is the in-service filter, can be used without being switched.

The time t20 is a first timing for judging indications of degradation in the performance of the first adaptive filter 202a, which is the in-service adaptive filter. The time t30 (first time point) is a first timing for judging that there are indications of degradation of the first adaptive filter 202a.

The a priori adaptive processing of the second adaptive filter 202b, which is the next adaptive filter to be used, is started at time t30 (first time point). The time t40 (second time point) is the time point at which a predetermined time has elapsed from the time t30 (first time point) and the preparation (standby) of the second adaptive filter 202b, which is the next adaptive filter to be used, is completed.

The third interval TZ from the time t30 (first time point) to the time t40 (second time point) is the interval in which the a priori adaptive processing of the second adaptive filter 202b continues.

The second interval TY, which is the interval in which the first adaptive filter 202a continuously operates, ends at the time t40 (second time point), and at this time point, the filter that is actually being used is switched from the first adaptive filter 202a to the second adaptive filter 202b.

The second adaptive filter 202b, which is the next adaptive filter to be used, is already in an advantageous state immediately after switching adaptive filters; therefore, self-adaptation progresses so as to capture the pulse signal. Therefore, in the present embodiment, the performance of the adaptive filter that is actually being used can continuously be kept at an advantageous level.

The timings from the time t10 to the time t50 can be easily managed and readily implemented by the timing determination section (timer) 216 (see FIG. 1).

Figure 5:
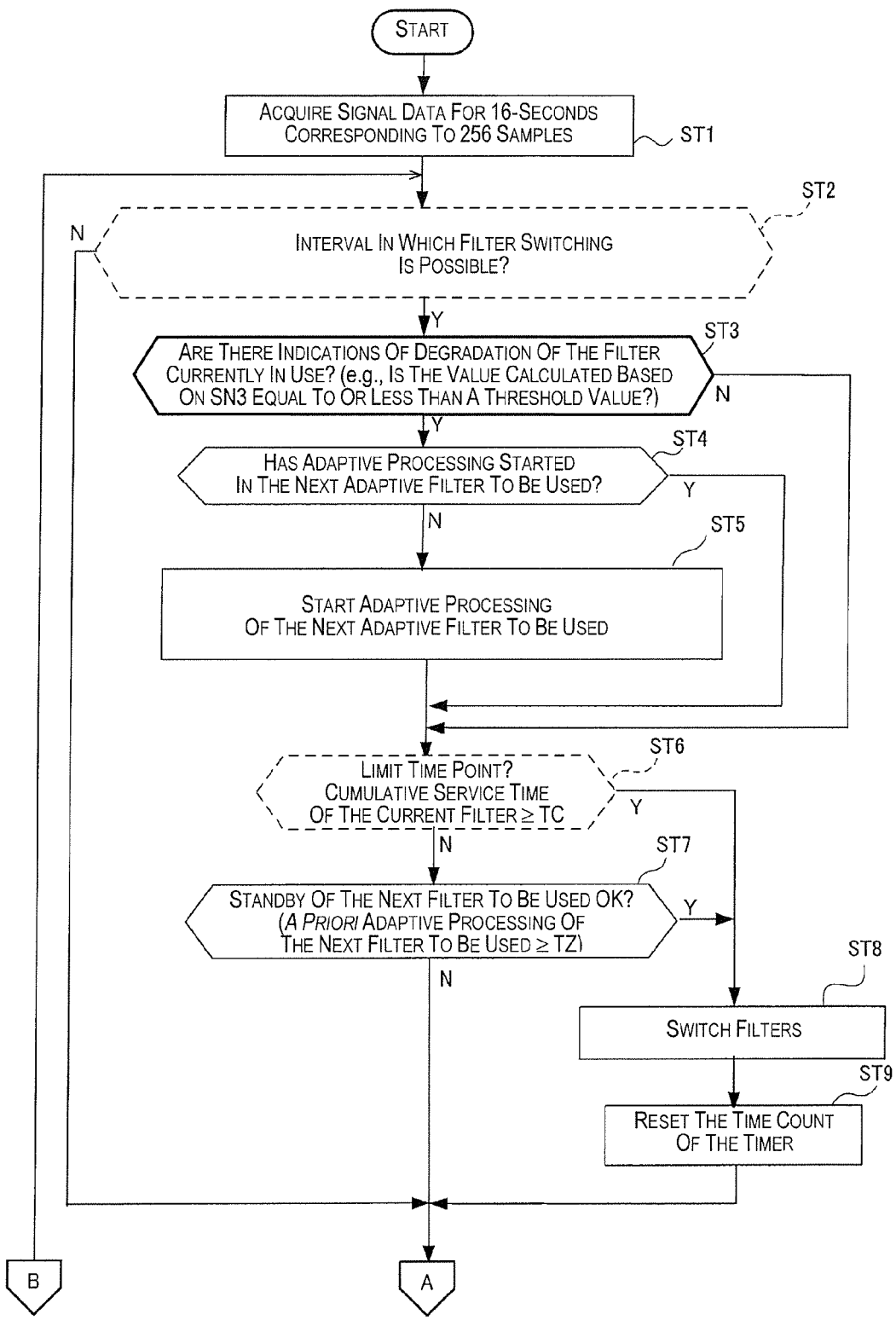
FIG. 5 is a flowchart showing a procedural example of the process for switching adaptive filters.

A Specific Example of the Processing Procedure for Switching the Adaptive Filters FIG. 5 is a flowchart showing a procedural example of the process for switching adaptive filters. First, a 16-second signal (pulse wave signal data or the like) that corresponds to 256 samples is acquired (step ST1). Next, it is determined whether the interval is one that allows the adaptive filters to be switched (step ST2). However, step ST2 can be omitted. In the case that the interval is determined not to be one that allows the adaptive filters to be switched (No, in step ST2), the flow proceeds to a later-described step ST10.

Next, in the case that the interval is determined to be one that allows the adaptive filters to be switched (Yes, in step ST2), it is judged whether there are indications of degradation of the adaptive filter currently being used (step ST3). This judgment can use a method that, e.g., detects whether the value calculated on the basis of SN3 is equal to or less than a threshold value as described above.

When indications of degradation of the adaptive filter have been detected (Yes, in step ST3), it is determined whether the adaptive processing of the next adaptive filter to be used has already started (step ST4), and if not yet started (N, in step ST4), the adaptive processing of the next adaptive filter to be used is started. The next adaptive filter to be used is in an initialized state or in the state of an advantageous time point in the past, and a priori adaptive processing is started from this state (step ST5).

The flow proceeds to step ST6 in the case that N is the result in step ST3 and in the case that Y is the result in step ST4.

In step ST6, it is judged whether the limit time point has been reached, the limit time point being the time point at which the adaptive filter is forcibly switched. For example, it is judged whether the cumulative service time of the in-service adaptive filter has reached a time that corresponds to the permissible time TC. However, step ST6 can be omitted.

In the case that N is the result in step ST6, it is determined whether the preparation of the next adaptive filter to be used is completed (step ST7). For example, if the a priori adaptive processing time has reached a time that corresponds to the third interval TZ, it is judged that preparation is complete (standby OK).

In the case that Y is the result in steps ST6 and ST7, processing for switching the filters is carried out (step ST8), the time count of the timing determination section (timer) 216 is reset, and a new time count is started (step ST9). The flow then progresses to the next process A. In the case that Y is the result in steps ST6 and ST7, the flow progresses to the next process A.

Described next are the procedures for the adaptive filtering process (preprocessing carried out by the pulse wave signal filtering section 200 prior to frequency analysis) and the frequency analysis process (post-processing) carried out by the pulse wave frequency analyzer 400.

Figure 6:
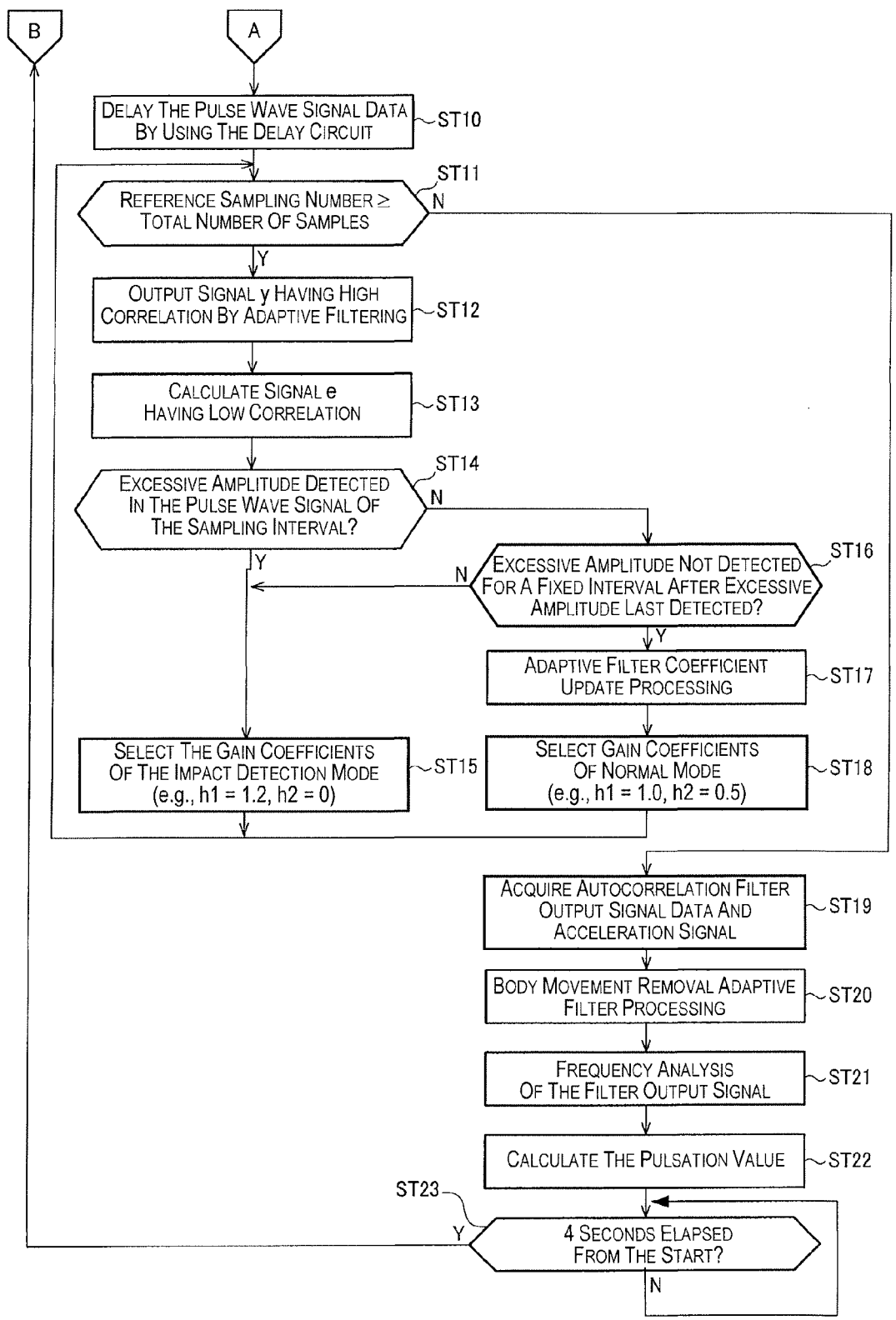
FIG. 6 is a flowchart showing an example of the procedures of the adaptive filtering process (preprocessing) and the frequency analysis process (post-processing)

FIG. 6 is a flowchart showing an example of the procedures of the adaptive filtering process (preprocessing) and the frequency analysis process (post-processing). In preprocessing, the pulse wave signal d is first delayed by the delay processor 201 (step ST10). Next, it is judged whether the quantity of data thus processed has reached the total number of samples (step ST11), and in the case that the total number of samples has not been reached (Yes, in step ST11), processing is carried out by the first adaptive filter 202a or the second adaptive filter 202b, and a first signal (constant component) y, which is a signal with high autocorrelation, is outputted (step ST12). Next, the first signal y is subtracted from the pulse wave signal d, whereby a signal e having low autocorrelation is outputted (step ST13). In the case that the quantity of processed data is determined to have reached the total number of samples in step ST11 (N, in step ST11), the flow proceeds to a later-described step ST19.

Subsequent to step ST13, it is determined whether excessive amplitude has been detected in the pulse wave signal during the sampling interval (step ST14). In the case that an excessive amplitude has been detected (Yes, in step ST14), gain coefficients (e.g., h1=1.2, h2=0) of the impact detection mode is selected because there is a high possibility that an impact noise has been applied, and an output value is calculated on the basis of the selected gain coefficients (step ST15). The flow thereafter returns to step ST11 and continues processing.

In the case that an excessive amplitude is not detected in step ST14 (N, in step ST14), it is determined whether an excessive amplitude has not been detected for a fixed interval after the excessive amplitude was last detected (step ST16), and if an excessive amplitude has not been detected (Yes, in step ST16), the adaptive filter coefficient update process is carried out (step ST17). In the case that it has been determined that an excessive amplitude has been detected in a fixed interval in step ST16 after excessive amplitude was last detected (N, in step ST16), the process proceeds to step ST15. After step ST 17, gain coefficients (for example, h1=1.0, h2=0.5) of the normal mode is selected and an output value is calculated on the basis of the selected gain coefficients (step ST18). The flow thereafter returns to step ST11 and continues processing.

The procedures of post-processing are described next. First, a filtered signal and an acceleration signal or the like (body movement signal) are acquired (step ST19). Next, a body movement removal adaptive filtering process is carried out (step ST20) by the body movement noise removal processor 300 (see FIG. 1).

Next, a frequency analysis process is carried out by the pulse wave frequency analyzer 400 (step ST21). A pulse rate (pulsation value) is subsequently calculated by the pulsation count calculation section 410 (step ST22).

Next, it is determined in step ST23 whether four seconds (sample period of the pulse wave signal) have elapsed, and if four seconds have elapsed (Yes, in step ST23), the flow returns to step ST2. In the case that it has been determined in step ST23 that four seconds have not elapsed (N, in step ST23), the flow loops in step ST23 until it has been determined that four seconds have elapsed.

Actual Processing Example

An actual processing example is described below. FIG. 7 is a view showing an example of judging filter degradation indications using SN3.

In the example of FIG. 7, indications of filter degradation are determined on the basis of a comparison of the values (first values) of SN3 that are based on the pre-filtering pulse wave signal (original signal) d and the values (second values) of SN3 that are based on the filtered signal (the filtered pulse wave signal). More specifically, it is ascertained that there is a filter performance degradation trend in the case that the difference between average values is less than a threshold value, the average values being the average value (e.g., the simple arithmetic average value) of the most recent single minute of values (first values) of SN3 that are based on the pre-filtering pulse wave signal d and the average value (e.g., the simple arithmetic average value) of the values of the most recent single minute of the values (second values) of SN3 that are based on the filtered signal (the filtered pulse wave signal).

Shown in table format (data table format) in FIG. 7 are an example of the values (first values) of SN3 that are based on the pre-filtering pulse wave signal d, an example of the average value of the most recent single minute thereof, an example of the values (second values) of SN3 that are based on the filtered pulse wave signal, and an example of the average value of the most recent single minute thereof.

In the example of FIG. 7, the following relationship holds true as shown above the table. In other words, 0.156718–0.117115≈0.0396<0.04 holds true.

Here, 0.156718 is the average value of the values of the most recent single minute of the values (second value) of SN3 that is based on the filtered pulse wave signal; 0.117115 is the average value of the most recent single minute of the values (first value) of SN3 that is based on the filtered pulse wave signal; and 0.0396 is the difference of the average values. The determination threshold value is 0.04 (i.e., 4%).

In this example, the differential value of the average values of SN3 for a single minute is less than 4%, and the performance of the adaptive filter is therefore determined to have started degrading.

In other words, if the filtering process is being properly carried out, the differential value obtained by subtracting the average value of second values of from the average value of the first values of should be equal to or greater than a predetermined threshold value. A differential value that is less than the threshold value means that there is little difference between the state of the spectrum of the filtered signal and the state of the spectrum of the pre-filtering signal, and in this case, a conjecture can be drawn that the adaptive filter is not working effectively and it can therefore be determined that there are indications of performance degradation of the adaptive filter. In this manner, indications of degradation of the in-service adaptive filter can be detected with good precision.

However, this determination example is a single example, and no limitation is imposed thereby. The above-described determination can be carried out continuously over three minutes, and if the difference (differential value) of the average values of SN3 is less than 4% of the determination threshold value for a predetermined consecutive number of cycles (e.g., three cycles), it can be determined that there are indications of performance degradation of the adaptive filter.

Instead of the differential value as described above, it is possible to compare, e.g., independent values of the average values of SN3 with the threshold value to judge indications of degradation of the adaptive filter.

Figure 8A:
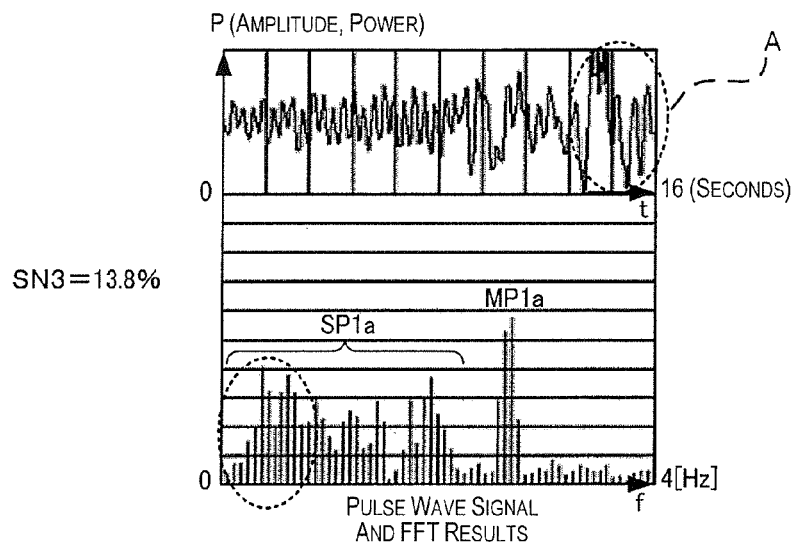
FIGS. 8A to 8C are views showing an example of the pulse wave signal waveform in actual processing, and the frequency spectrum obtained by FFT.
Figure 8B:
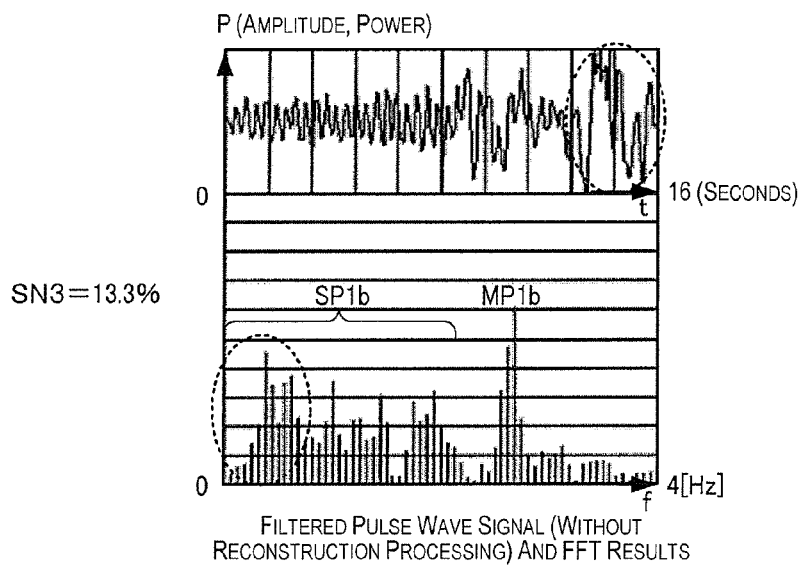
Figure 8C:
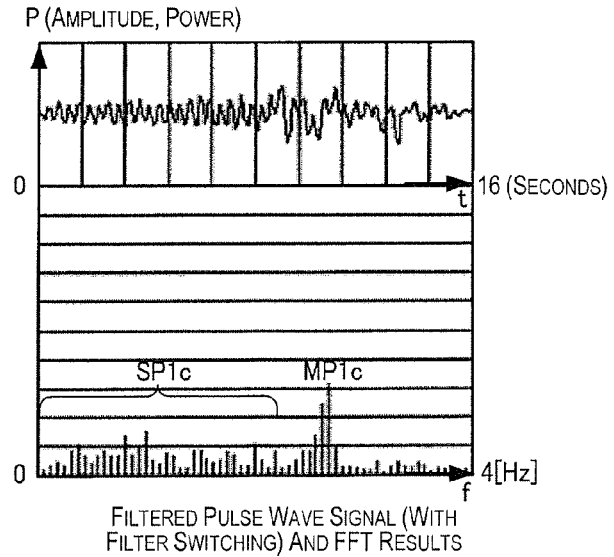

FIGS. 8A to 8C are views showing an example of the pulse wave signal waveform in actual processing, and the frequency spectrum obtained by FFT. FIG. 8 shows the waveform (upper part) of 16 minutes of the pulse wave signal, and the FFT results (lower part) thereof. The pulse wave signal used in this example is a pulse wave signal obtained when walking, jogging, or another activity is not being performed.

In the waveform of the upper part of FIG. 8A, intermixing of a signal thought to be an external noise component can be seen in the vicinity of terminal portion of 16 seconds of the signal (portion A surrounded by the dotted line). In the FFT results of the lower part, a pulse signal component MP1$a$, which is the detection target component, and an external noise signal component SP1$a$ are intermixed in the pulse wave signal.

Next, reference will be made to FIG. 8B. FIG. 8B shows the pulse wave signal obtained by filtering the pulse wave signal having the waveform shown in the upper part of FIG. 8A by using an adaptive filter that has not undergone adaptive filter switching; and shows the FFT results thereof. Here, the adaptive filter is in a state of continuous operation for about 40 minutes from the start of measurement (a state of having been used while the filter coefficients have been updated). However, the filter switching process has not been carried out.

It is apparent from FIG. 8B that the external noise component (noise signal component) SP1$b$ remains uncut. In the example of FIG. 8B, it is possible that, by chance, the signal MP1$b$ will be determined to be the pulse-presenting spectrum by a sorting process (a process for arranging the plurality of spectra in order from large peak values) that is based on the peak values of the spectra, because the spectrum value of the pulse-presenting spectrum MP1$b$ is the largest value. However, in the case that the pulse-presenting spectrum MP1$b$ is small, it is difficult to differentiate from the external noise component (noise signal component) SP1$b$, and there is a high possibility that detection of the pulse component will not be successful.

Next, reference will be made to FIG. 8C. FIG. 8C shows the pulse wave signal obtained by filtering the pulse wave signal having the waveform shown in the upper part of FIG. 8A by using the adaptive filters 202; and shows the FFT results thereof. Here, the adaptive filters 202 are in a state of continuous operation for about 40 minutes from the start of measurement (a state of having been used while the filter coefficients have been updated), and the adaptive filters have been switched at 10 minute intervals.

It is apparent from FIG. 8C that the external noise component SP1$c$ has been sufficiently suppressed by the adaptive filtering process, while the pulse-presenting spectrum MP1$b$ has been accentuated and the pulse component can thereby be reliably identified.

The S/N index (i.e., SN3) in the pulse wave signal (original signal) shown in FIG. 8A is 13.8%. SN3 in the pulse wave signal (without switching adaptive filters) shown in FIG. 8B is 13.3% and is slightly lower than the original signal. In contrast, SN3 in the pulse wave signal (with switching adaptive filters) shown in FIG. 8C is 18.7% and S/N is considerably improved. The effect of switching the first adaptive filter 202$a$ and the second adaptive filter 202$b$ can be numerically confirmed due to the fact of this S/N improvement.

Second Embodiment

Figure 9A:
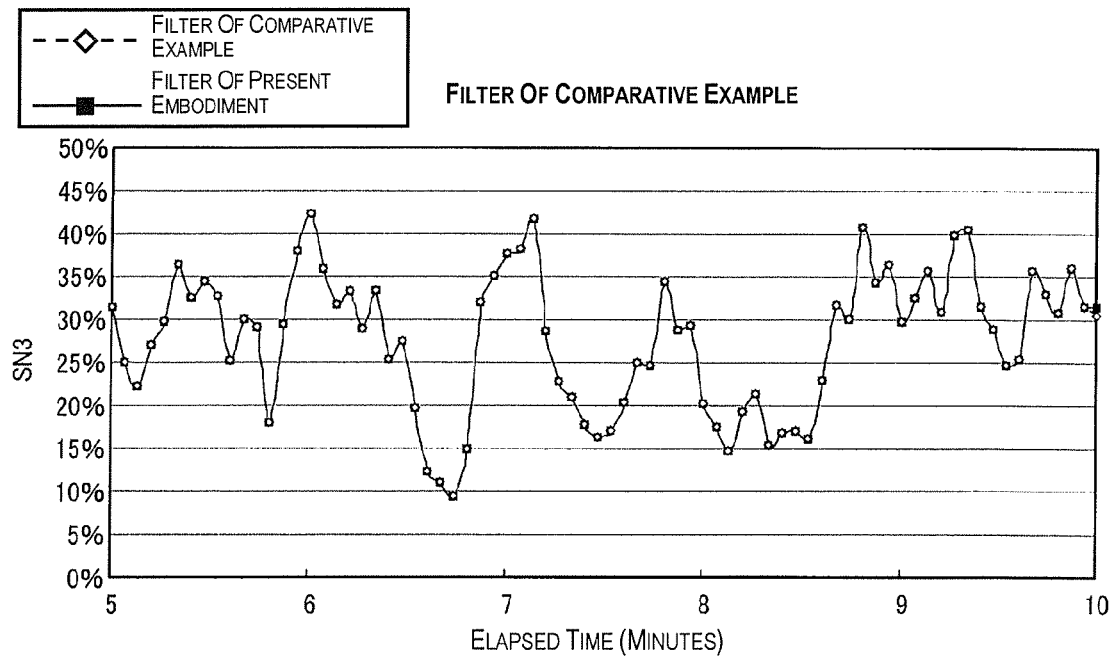
FIGS. 9A and 9B are views showing the result of examining fluctuation of the S/N index (SN3) in each example of switching adaptive filters and an example without switching (comparative example) in response to elapsed time.
Figure 9B:
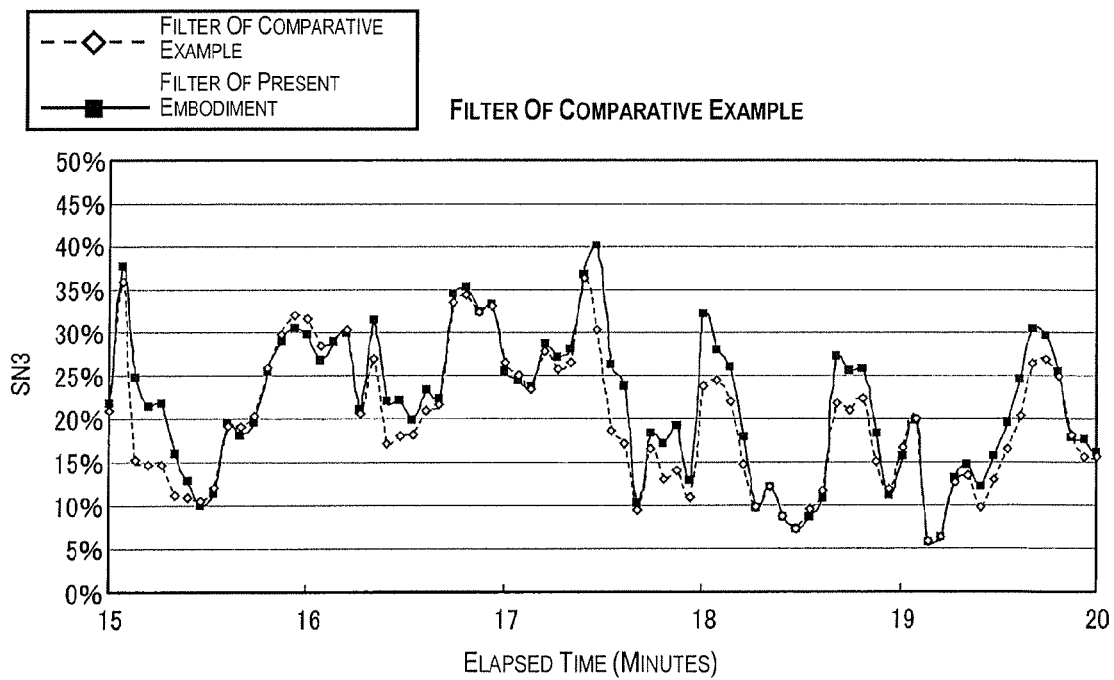

FIGS. 9A and 9B are views showing the result of examining fluctuation of the S/N index (SN3) in each example of switching adaptive filters and in an example without switching (comparative example) in response to elapsed time.

Here, a subject wears the wristwatch-type pulse rate meter (i.e., pulse detector 100), and walks for 20 minutes. The pulse wave signal is filtered by the adaptive filters, the S/N index (SN3) is calculated for the filtered signal, and the calculation results are plotted on the time axis.

In FIGS. 9A and 9B, the horizontal axis is the time axis, and the vertical axis is an axis showing the values (%) of SN3, which is the S/N index. FIG. 9A shows the change in SN3 over time until 10 minutes have elapsed from the start of walking by the user as the subject. FIG. 9B shows the change in SN3 over time until 20 minutes have elapsed from a time point at which 15 minutes have elapsed. Also, the data that corresponds to the present embodiment is shown by black squares, and the data of the comparative example is shown by white diamond shapes.

There is substantially no difference in the SN3 values between the present embodiment and the comparative example from the start of measurement until the time point at which about 10 minutes have elapsed (FIG. 9A). However, it is apparent from FIG. 9B that there is a clear difference by about 15 minutes of elapsed time. It is apparent that the present embodiment in which the adaptive filters are switched has higher SN3 values when viewed overall.

FIGS. 9A and 9B demonstrate that the performance of the adaptive filter actually being used can be constantly kept at a suitable level by switching with suitable timing the adaptive filters 202 constituting the pulse wave signal filtering section. Therefore, the performance of the adaptive filters can be kept at a suitable level even when continuous measurement is carried out for a long period of time. For example, the performance of the adaptive filters can be kept at a suitable level even when continuous measurement is carried out for a long period of time. Therefore, it is thereby possible to reduce the occurrence pulse detection failures and detection errors.

For example, the filter configuration can be simplified because the adaptive filters are effectively used, and the adaptive filters are readily switched. It is therefore possible to realize a pulse detector that can, e.g., carry out effective noise countermeasures while the processing load of the device is reduced.

The present embodiment was described in detail above, and it is readily apparent to a person skilled in the art that various modifications can be made without substantively departing from the novel features and effects of the invention. Therefore, any such modifications are understood to reside within the scope of the invention.

For example, it is also possible to provide two or more adaptive filters and use the adaptive filters in a time-divided manner (i.e., while being switched as appropriate). In the specification and drawings, terms described together with different terms that are broader in meaning or synonymous can replace the different terms at least once in any location in the specification and drawings.

What is claimed is:

1. A pulse detector that detects a pulse signal that originates from a pulse of a subject, the pulse detector, comprising:
    a pulse wave sensor that outputs a pulse wave signal in which are intermixed the pulse signal and a noise signal including a body movement noise signal originating in the body movement of the subject;
    a pulse wave signal filtering section having a first adaptive filter and a second adaptive filter that self-adaptively adjust a frequency response characteristic, the first and second adaptive filters being filters that filter the pulse wave signal, and an adaptive filter switching section that switches the adaptive filter to be used, where the switching occurs in a first interval in which the pulse wave sensor is continuously operating; and a pulse wave frequency analyzer that performs a frequency analysis process at predetermined time intervals on the basis of a filtered signal outputted from the pulse wave signal filtering section and identifying a pulse-presenting spectrum that shows the pulse signal, wherein at a first time point partway through a second interval in which the first adaptive filter is continuously carrying out adaptive processing, where the second interval occurs in the first interval, the adaptive filter switching section causes the second adaptive filter to start adaptive processing, and switches from the first adaptive filter to the second adaptive filter at a second time point that is a time point after the first time point and is the end point of the second interval.

2. The pulse detector according to claim 1, wherein when the adaptive processing of the second adaptive filter is started, the adaptive filter switching section starts the adaptive processing from a state in which a filter coefficient has been initialized, or a state in which the filter coefficient has been set to a filter coefficient value of a time point in an interval in which the second adaptive filter had been operating continuously in the past.

3. The pulse detector according to claim 1, wherein the adaptive filter switching section has an adaptive filter performance evaluation section that evaluates the performance of the first adaptive filter; and the first time point is a time point at which the performance of the first adaptive filter is evaluated to have degraded by the adaptive filter performance evaluation section.

4. The pulse detector according to claim 3, wherein the adaptive filter performance evaluation section evaluates the performance of the first adaptive filter on the basis of an index calculated on the basis of a frequency spectrum of at least one signal among the pulse wave signal prior to filtering by the pulse wave signal filtering section and the filtered signal outputted from the pulse wave signal filtering section.

5. The pulse detector according to claim 4, wherein the index is an index obtained by using the total value of the frequency spectrum appearing in the entire observed frequency band to divide the total of the value of the pulse-presenting spectrum and the value for each of the left and right spectra appearing adjacent to the pulse-presenting spectrum on the frequency axis; and the adaptive filter performance evaluation section evaluates the performance of the first adaptive filter by comparing a first value of the index obtained on the basis of the pulse wave signal before filtering by the pulse wave signal filtering section, and a second value of the index obtained on the basis of the filtered signal outputted from the pulse wave signal filtering section.

6. The pulse detector according to claim 1, wherein the second time point is a time point at which a predetermined time has elapsed from the first time point.

7. The pulse detector according to claim 1, wherein the second time point is a time point at which a predetermined permissible time has elapsed from a third time point, which is the time point at which the second interval started.

8. The pulse detector according to claim 1, wherein the pulse wave signal filtering section includes a delay processor that delays the pulse wave signal by a predetermined time, a filter coefficient update section that updates the coefficient of at least one of the first adaptive filter and the second adaptive filter, and a subtractor;

at least one of the first adaptive filter and the second adaptive filter outputs a first signal having high autocorrelation from among the output signals of the delay processor;

the subtractor subtracts the first signal from the pulse wave signal, generates a second signal having lower autocorrelation than the first signal, and feeds the second signal to the filter coefficient update section; and the filter coefficient update section updates the coefficient of at least one of the first adaptive filter and the second adaptive filter so that the second signal is suppressed.

* * * * *